United States Patent
Okuno et al.

(10) Patent No.: US 12,249,438 B2
(45) Date of Patent: Mar. 11, 2025

(54) BEAM TARGET AND BEAM TARGET SYSTEM

(71) Applicant: RIKEN, Wako (JP)

(72) Inventors: Hiroki Okuno, Wako (JP); Naoya Furutachi, Wako (JP); Yoshiharu Mori, Wako (JP)

(73) Assignee: RIKEN, Wako (JP)

( * ) Notice: Subject to any disclaimer, the term of this patent is extended or adjusted under 35 U.S.C. 154(b) by 651 days.

(21) Appl. No.: 17/434,689

(22) PCT Filed: Feb. 3, 2020

(86) PCT No.: PCT/JP2020/003988
§ 371 (c)(1),
(2) Date: Aug. 27, 2021

(87) PCT Pub. No.: WO2020/175027
PCT Pub. Date: Sep. 3, 2020

(65) Prior Publication Data
US 2022/0165446 A1    May 26, 2022

(30) Foreign Application Priority Data
Feb. 28, 2019   (JP) .................................. 2019-036815

(51) Int. Cl.
*G21G 1/06*     (2006.01)
*G21G 1/10*     (2006.01)
(Continued)

(52) U.S. Cl.
CPC ................. *G21G 1/06* (2013.01); *G21G 1/10* (2013.01); *G21G 4/02* (2013.01); *G21K 5/08* (2013.01);
(Continued)

(58) Field of Classification Search
CPC .. H05H 3/06; H05H 6/00; G21G 4/02; G21G 1/10; G21G 1/02; G21G 1/04; G21G 1/06;
(Continued)

(56) References Cited

U.S. PATENT DOCUMENTS 3,349,001 A * 10/1967 Stanton .................... G21C 1/30
                                                    976/DIG. 34
3,453,175 A    7/1969 Hodge
(Continued)

FOREIGN PATENT DOCUMENTS

CN    103096610 A     5/2013
JP    2002221600 A  * 8/2002
(Continued)

OTHER PUBLICATIONS

Bauer, G. S., M. Salvatores, and G. Heusener. "MEGAPIE, a 1 MW pilot experiment for a liquid metal spallation target." Journal of Nuclear Materials 296.1-3 (2001): 17-33. (Year: 2001).*
(Continued)

*Primary Examiner* — Sharon M Davis
(74) *Attorney, Agent, or Firm* — Birch, Stewart, Kolasch & Birch, LLP

(57) ABSTRACT

A beam target for generating a nuclear reaction product by irradiation with a beam obtained from a beam generation source includes a cone body which has a tapered inner surface which is reduced in diameter toward a tip, and supply means for supplying liquid metal to the inner surface of the cone body to form a liquid film of the liquid metal on the inner surface. It is possible to form the liquid film of the liquid metal on a cone body surface to increase an irradiation area of the beam, and also dispose a target substance such as LLFP around the cone body, and hence it is possible to (Continued)

efficiently use the nuclear reaction product (e.g., a neutron) generated by beam irradiation of the liquid metal.

6 Claims, 8 Drawing Sheets

(51) Int. Cl.
    *G21G 4/02*     (2006.01)
    *G21K 5/08*     (2006.01)
    *H05H 6/00*     (2006.01)
    *A61N 5/10*     (2006.01)
    *G21K 5/04*     (2006.01)

(52) U.S. Cl.
    CPC .......... *H05H 6/00* (2013.01); *A61N 2005/109* (2013.01); *G21K 5/04* (2013.01)

(58) Field of Classification Search
    CPC ... G21K 5/08; G21K 5/04; G21C 1/30; G21B 1/01; G21B 1/13
    See application file for complete search history.

(56) References Cited

U.S. PATENT DOCUMENTS

| | | | | |
|---|---|---|---|---|
| 3,623,130 A * | 11/1971 | Dalrymple | ............... | H05H 6/00 376/192 |
| 5,160,696 A * | 11/1992 | Bowman | ................... | G21F 9/30 376/195 |
| 5,392,319 A * | 2/1995 | Eggers | ..................... | H05H 3/06 376/151 |
| 5,768,329 A | 6/1998 | Berwald | | |
| 2003/0156675 A1* | 8/2003 | Venneri | .................... | G21G 1/10 376/189 |
| 2005/0082469 A1* | 4/2005 | Carlo | ....................... | G21G 1/06 250/262 |
| 2008/0237499 A1* | 10/2008 | Auchterlonie | .......... | H05H 1/46 250/503.1 |
| 2018/0160521 A1* | 6/2018 | Hsueh Liu | ............. | H05H 7/001 |
| 2018/0218799 A1* | 8/2018 | Mofakhami | ............. | H05H 3/06 |

FOREIGN PATENT DOCUMENTS

| | | |
|---|---|---|
| JP | 2002-258000 A | 9/2002 |
| JP | 2018-72211 A | 5/2018 |

OTHER PUBLICATIONS

Chinese Office Action and Search Report for Chinese Application No. 202080017239.3, dated Nov. 9, 2023, with an English translation.

Extended European Search Report for corresponding European Application No. 20763499.9, dated Oct. 17, 2022.

International Search Report for PCT/JP2020/003988 (PCT/ISA/210) mailed on Mar. 31, 2020.

Kondo et al., "IFMIF/EVEDA lithium test loop: design and fabrication technology of target assembly as a key component", Nuclear Fusion, 2011, vol. 51, #123008, pp. 1-12.

Willis et al., "High-power lithium target for accelerator-based BNCT", Proceedings of LINAC08, Proton and Ion Accelerators and Applications, 2008, Monday Poster Session 063, pp. 223-225.

Woloshun et al., "Comparison of 2 Lead-Bismuth Spallation Neutron Targets", Princeton University, Department of Physics, Princeton Muon Collider Technical Notes, Muon Collider Targetry and Phase Rotation, Index of /mumu/target/pb-bi, Dec. 12, 2001, http://www.hep.princeton.edu/mumu/target/pb-bi/, total of 12 pages.

Written Opinion of the International Searching Authority for PCT/JP2020/003988 (PCT/ISA/237) mailed on Mar. 31, 2020.

Korean Office Action (including an English translation thereof) issued in the corresponding Korean Patent Application No. 10-2021-7028036 on Jan. 3, 2025.

\* cited by examiner

[Fig. 4]
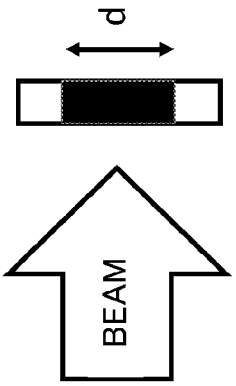
FIG. 4A COMPARATIVE EXAMPLE 1 (FREE FALL)
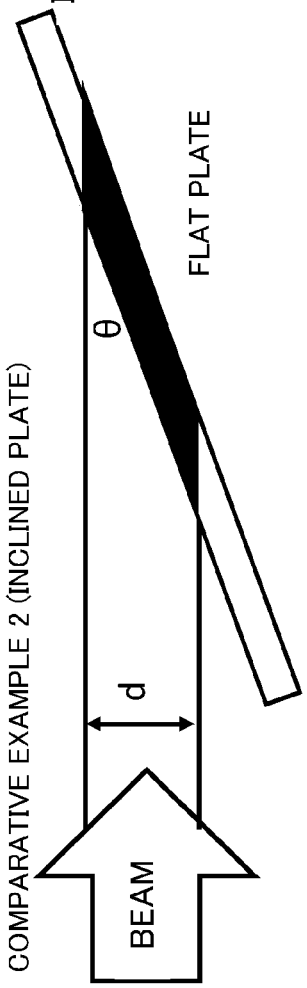
FIG. 4B COMPARATIVE EXAMPLE 2 (INCLINED PLATE)
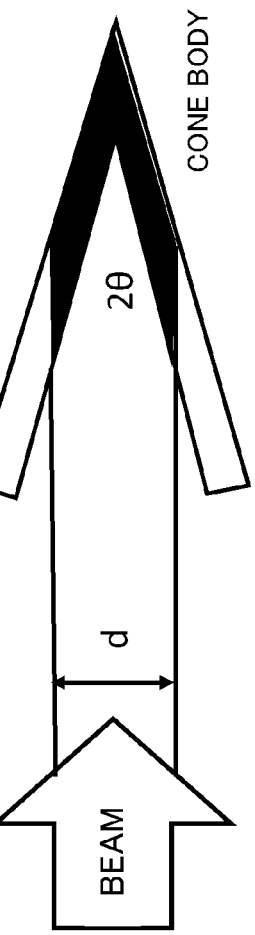
FIG. 4C PRESENT METHOD (CONE BODY)

[Fig. 5]
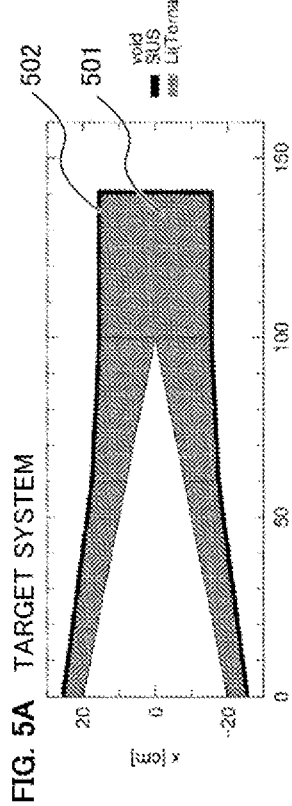
FIG. 5A TARGET SYSTEM
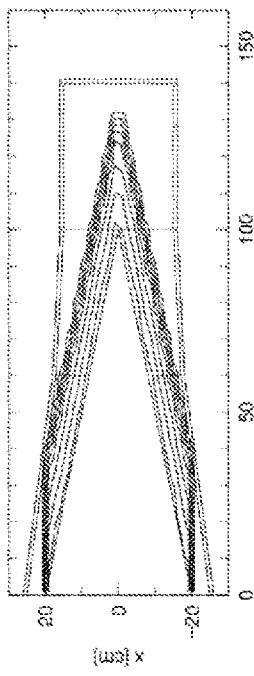
FIG. 5B DEUTERON BEAM TRACK
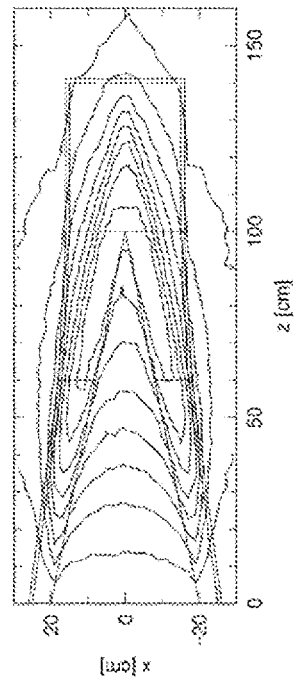
FIG. 5C NEUTRON TRACK
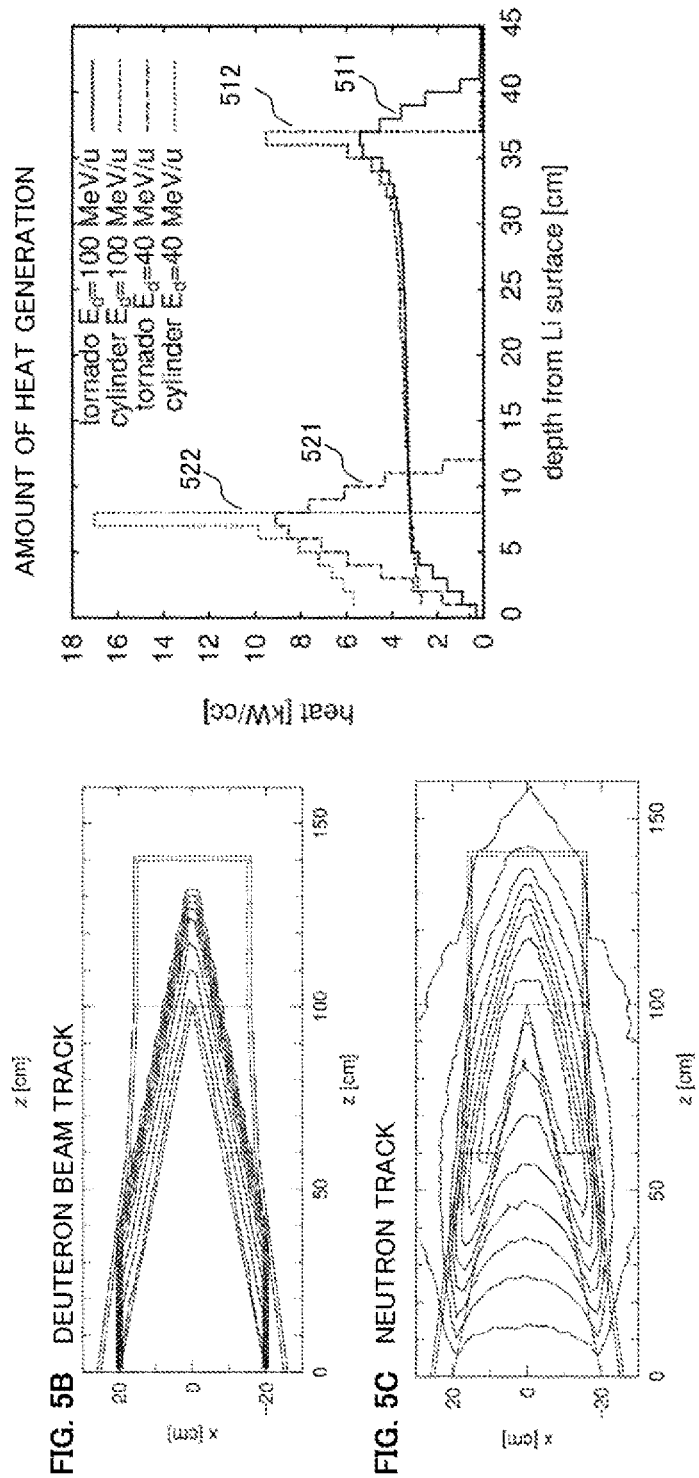
FIG. 5D AMOUNT OF HEAT GENERATION

[Fig. 6]
FIG. 6A LLFP PLACEMENT
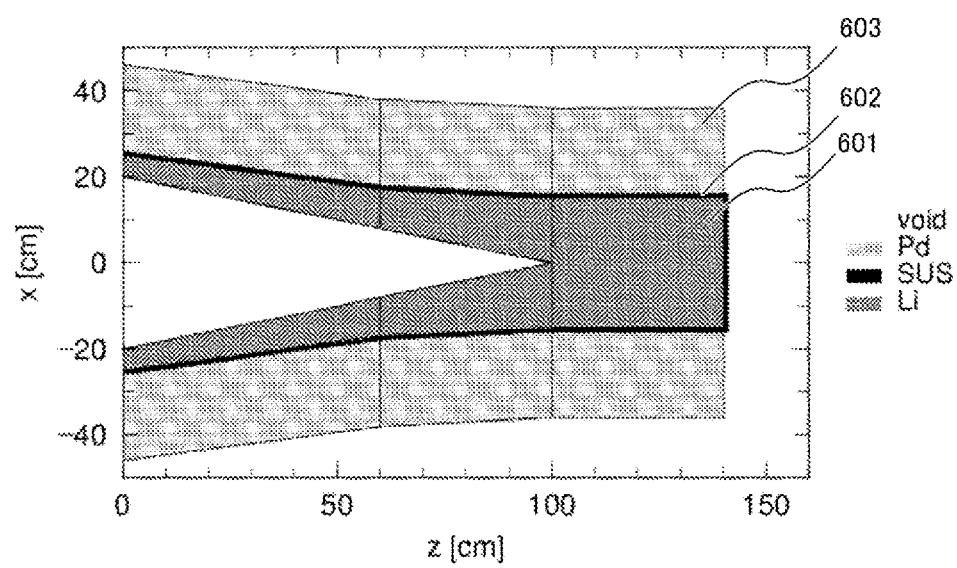
FIG. 6B ENERGY DISTRIBUTION OF NEUTRON EMITTED TO OUTSIDE OF TARGET
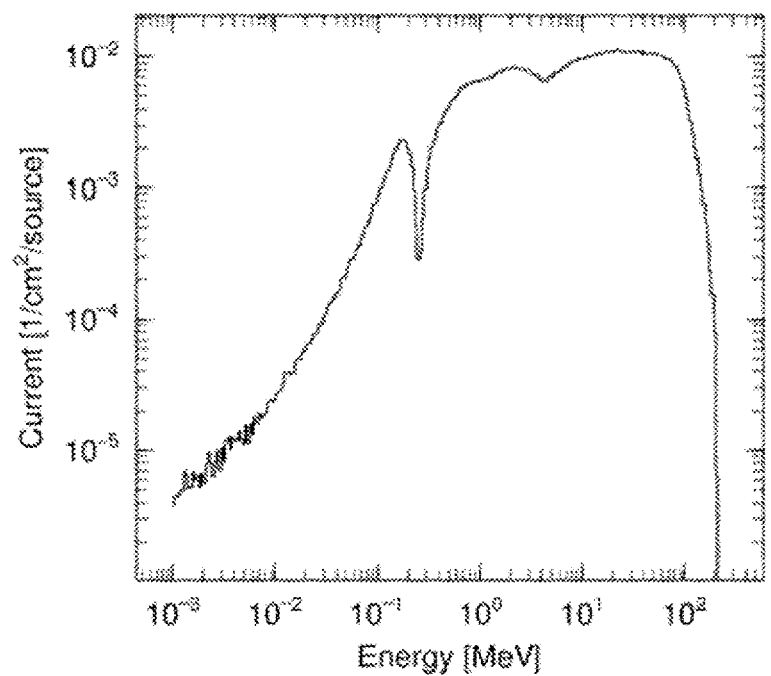

BEAM TARGET AND BEAM TARGET SYSTEM

TECHNICAL FIELD

The present invention relates to a beam target and a beam target system.

BACKGROUND ART

A beam target system is used for irradiating metal or the like serving as a target with a high-intensity charged particle beam to generate a neutron. The generated neutron is used in nuclear transmutation of long lived fission products (LLFP), evaluation of a fusion reactor material, boron neutron capture therapy (BNCT), and non-destructive inspection. In addition, the beam target system is also used for generating a nuclear reaction product such as astatine-211 which is expected to be used as an RI for α-ray internal therapy by irradiation with the charged particle beam.

When the intensity of the beam to be emitted is increased, a thermal load at a beam target becomes a problem. PTL 1 proposes removal of generated heat by circulating liquid metal in a vessel. Note that, in the case of this method, a beam is emitted via a beam window (solid) of the vessel, and hence a problem arises in that the beam window is damaged.

In contrast to this, in NPL 1, it is proposed to generate a liquid film by a free surface flow by causing liquid metal to flow along a curved plate, and directly irradiate the liquid film with a beam. A flow path of the liquid metal is curved, and hence the pressure of the liquid is increased by centrifugal force, and it is possible to prevent boiling inside the liquid metal liquid film. In addition, it is also proposed to incline the liquid film with respect to a beam irradiation direction in order to increase an irradiation area.

CITATION LIST

Patent Literature

[PTL 1] Japanese Patent Application Publication No. 2018-72211

Non Patent Literature

[NPL 1] Kondo, H., et al. "IFMIF/EVEDA lithium test loop: design and fabrication technology of target assembly as a key component." Nuclear Fusion 51. 12 (2011): 123008.

SUMMARY OF INVENTION

Technical Problem

In the case where a nuclear reaction product (e.g., a neutron) which is generated by causing a beam to collide with a target is used, it is important to be able to efficiently dispose an irradiation target (e.g., the LLFP or an examination • therapy portion) of the nuclear reaction product in the vicinity of the target. In the method of NPL 1, an irradiation target object of the nuclear reaction product can be installed only behind the curved plate, and hence the method is not efficient. In the case where the liquid film is inclined and used as well, space in which the irradiation target object is disposed is limited, and hence the method is not efficient.

In view of the above problem, an object of the present invention is to provide a beam target capable of receiving a high-intensity beam, and a beam target system capable of efficiently using a generated nuclear reaction product.

Solution to Problem

An aspect of the present invention is a beam target for generating a nuclear reaction product by irradiation with a beam obtained from a beam generation source, including: a cone body which has a tapered inner surface which is reduced in diameter toward a tip; and supply means for supplying liquid metal to the inner surface of the cone body to form a liquid film of the liquid metal on the inner surface.

The liquid metal supplied by the supply means helically flows on the inner surface (inner wall) of the cone body, and the liquid film is thereby formed. The surface of the liquid film to be formed is preferably conical. Accordingly, the cone body has the tapered inner surface which is reduced in diameter toward its tip portion with a side farther from a beam reception side used as the tip. The inner surface of the cone body has a substantially truncated conical shape and, more strictly speaking, a taper angle does not need to be constant, and a tapered shape in which the taper angle is gradually reduced, and a tapered shape in which the taper angle is gradually increased may also be adopted. The inner surface of the cone body may also be cylindrical at the extreme tip. In addition, the overall shape of the cone body is not particularly limited and, in the case where a neutron generated by the beam irradiation of the liquid metal is used outside, the cone body is preferably formed thinly such that the neutron is not intercepted.

According to the beam target of the present aspect, the liquid film of the liquid metal is formed on the surface of the cone body having the tapered or truncated conical inner surface, and hence it is possible to increase a surface area (hereinafter referred to as an irradiation area) of the liquid film which is irradiated with the beam while maintaining the short length of the beam target. Note that it is possible to increase the irradiation area of the beam even by causing the liquid metal to flow on an inclined flat plate, but the total length of the target is increased. The beam target according to the present aspect is capable of increasing the irradiation area while reducing the total length.

In addition, in the beam target according to the present aspect, the liquid metal flows inside the cone body, and hence it is possible to dispose another object at any position outside the cone body. When the nuclear reaction product (e.g., the neutron) generated by the beam irradiation of the liquid metal is used for irradiating a substance outside the beam target, it is possible to dispose a target object in an entire area around the cone body, and hence it is possible to increase use efficiency of the nuclear reaction product. For example, in the case where LLFP or the like is subjected to nuclear transmutation by using the neutron generated by the irradiation with the beam applied to the liquid metal, it is possible to hold a target substance (e.g., the LLFP) to be subjected to the nuclear transmutation by irradiation with the neutron around the cone body.

The liquid metal (target material) may be appropriately selected according to a use, and examples thereof include liquid lithium, liquid bismuth, liquid sodium, liquid mercury, and liquid lead bismuth. In addition, in order to facilitate liquid film formation with the liquid metal on the entire inner surface of the cone body, a plurality of the supply means may be provided.

Further, the liquid metal helically flows, and hence pressure inside the liquid meatal liquid film is increased by centrifugal force, and it is possible to prevent boiling caused by the beam irradiation. The flow is a helical flow, and hence it is possible to obtain centrifugal force larger than that when the liquid metal is caused to flow on a curved plate, and the effect of preventing boiling is further increased.

In addition, in the present aspect, the cone body may be constituted by a target substance to be subjected to nuclear transmutation (e.g., $^{93}$Zr). Herein, constituting the cone body by the target substance to be subjected to the nuclear transmutation means that the target substance to be subjected to the nuclear transmutation is included in a material constituting the cone body, and other materials may also be included. Further, in the present aspect, the liquid metal supplied by the supply means may contain powder of the target substance to be subjected to the nuclear transmutation. The neutron is generated by the irradiation with the beam applied to the liquid metal, and hence, by disposing the target substance to be subjected to the nuclear transmutation in the liquid metal or in the cone body, the target substance to be subjected to the nuclear transmutation can be positioned extremely close to the generation position of the neutron, and it is possible to increase the efficiency of the nuclear transmutation.

In addition, in the present aspect, a helical groove may be provided in the inner surface of the cone body. It is possible to stabilize the flow of the liquid metal with the helical groove.

Another aspect of the present invention is a beam target system including: the beam target described above; and irradiation means for irradiating the liquid film with a beam obtained from a beam generation source.

The irradiation means includes, e.g., a beam window (e.g., a plasma curtain or a liquid metal window), deflection means for deflecting a beam obtained from an accelerator serving as the beam generation source to guide the beam to the beam target, and adjustment means for adjusting a beam diameter.

In addition, in the present aspect, the beam target system may further include a holding unit which holds a target substance (e.g., the LLFP) to be subjected to nuclear transmutation with a neutron generated by irradiation with the beam applied to the liquid metal around the cone body. As described above, it is possible to dispose the target substance to be subjected to the nuclear transmutation around the cone body, and hence it is possible to increase use efficiency of the neutron. For example, by covering the entire cone body with the target substance to be subjected to the nuclear transmutation, it is possible to use the neutron generated in the beam target more efficiently.

The beam target system in the present aspect may include output means for outputting a neutron generated by irradiation with a beam applied to the liquid metal in a direction orthogonal to an irradiation direction of the beam. In addition, the beam target system may include a plurality of the output means. In the case where the generated neutron is used for non-destructive inspection or BNCT, flexibility in the installation of a target object is increased, and it is also possible to apply the neutron to a plurality of targets simultaneously.

Advantageous Effects of Invention

According to the present invention, it is possible to provide the beam target capable of receiving the high-intensity beam, and the beam target system capable of efficiently using the generated nuclear reaction product.

BRIEF DESCRIPTION OF DRAWINGS

FIGS. 4A to 4C are views for explaining that it is possible to increase a beam irradiation area in a target in an embodiment.

FIGS. 5A to 5D are views showing tracks of a deuteron beam and a generated neutron in the first embodiment, and a result of a simulation which determines an amount of heat generation caused by beam irradiation.

FIGS. 6A and 6B are views for explaining a simulation for evaluating nuclear transmutation efficiency of the LLFP in the first embodiment.

DESCRIPTION OF EMBODIMENTS

Hereinbelow, modes for carrying out the invention will be described with reference to the drawings, but the present invention is not limited thereto. Components of individual embodiments described below can be appropriately combined.

First Embodiment

The present embodiment is a beam target system 100 used in nuclear transmutation of long lived fission products (LLFP). The beam target system 100 generates a neutron by irradiating liquid lithium with a deuteron beam accelerated by an accelerator (e.g., about 100 MeV per nucleon), and performs nuclear transmutation on the LLFP with the generated neutron to detoxify the LLFP.

[Structure]

Figure 1:
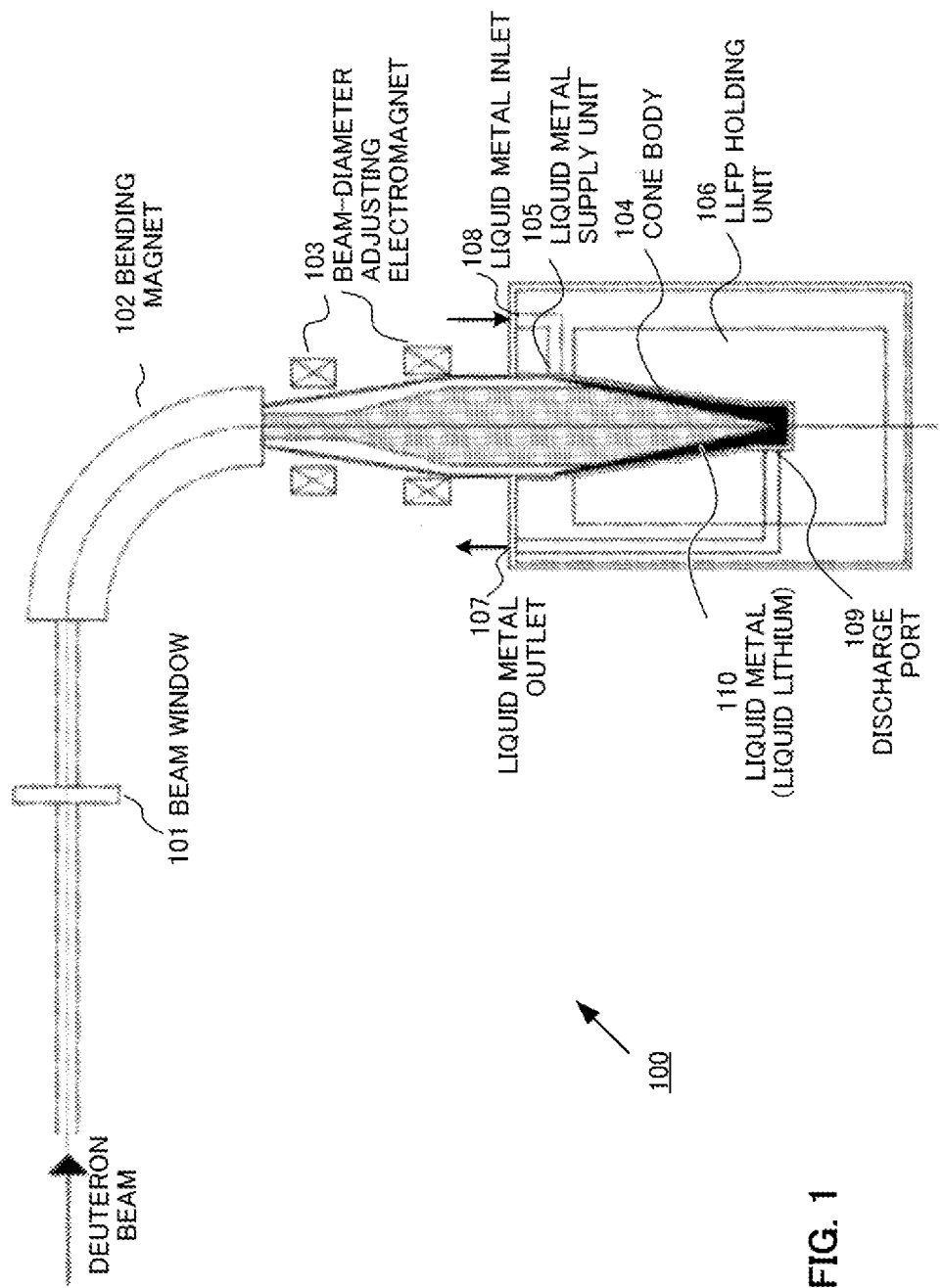
FIG. 1 is a view showing an overall structure of a beam target system (first embodiment) used for nuclear transmutation of LLFP.

FIG. 1 is a view showing an overall structure of the beam target system 100. As shown in the drawing, the beam target system 100 includes a beam window 101, a bending magnet 102, a beam-diameter adjusting electromagnet 103, a cone body 104, a liquid metal supply unit 105, and an LLFP holding unit 106.

The beam window 101 is a device which separates a high vacuum on an accelerator side from a beam target system side, and is constituted by a plasma curtain or a liquid metal window.

The bending magnet 102 changes a traveling direction of a deuteron beam. In the present embodiment, the direction of the deuteron beam is changed from a horizontal direction to a downward direction. The beam-diameter adjusting electromagnet 103 adjusts a beam diameter of the deuteron beam to a desired size. In the present embodiment, the beam diameter is 40 cm.

An inner surface of the cone body 104 has a substantially truncated conical shape which is reduced in diameter in a beam traveling direction, and an extreme tip side thereof is cylindrical. Note that, strictly speaking, the shape of the inner surface of the cone body 104 is not the truncated conical shape, but is a tapered shape in which a taper angle is reduced toward the tip thereof. The detail of the inner surface shape of the cone body 104 will be described later in detail by using FIG. 3.

The material of the cone body 104 may be any material as long as the material does not react with liquid metal (target material) chemically and has a certain strength, and it is possible to use, e.g., stainless steel (SUS).

The liquid metal supply unit 105 (hereinafter also referred to as a supply unit 105 simply) supplies liquid metal (liquid lithium in the present embodiment) such that velocity in a tangential direction is observed along the inner surface of the cone body 104 from an upper side of the cone body 104. Since the supply of the liquid metal which allows the observation of the velocity in the tangential direction is performed, it is possible to describe that the supply unit 105 jets the liquid metal. The liquid lithium produces a helical flow along the inner surface of the cone body 104, and forms a thin liquid film 110 on the inner surface. In FIG. 1, the liquid film (target) of the liquid metal formed on the inner surface of the cone body 104 is expressed by using black fill.

In order to stabilize the helical flow of the liquid metal, a groove extending along a helical flow path may be provided in the inner surface of the cone body 104.

A discharge port 109 for discharging the liquid metal is provided on a lower end side of the cone body 104, and the liquid metal is discharged from a liquid metal outlet 107 to the outside of the cone target. The discharged liquid metal is circulated by a circulation system 120 (see FIG. 2C) including a heat exchanger 121, an impurity removal device 122, and a circulation pump 123, and is resupplied from a fluid inlet 108 on an upper end side of the cone body 104.

The holding unit 106 holds the LLFP serving as a target substance to be subjected to the nuclear transmutation with the generated neutron. Examples of the LLFP include palladium-107 ($^{107}$pd), cesium-135 ($^{135}$Cs), zirconium-93 ($^{93}$Zr), and selenium-79 ($^{79}$Se). The LLFP held by the holding unit 106 is in contact with an outer surface of the cone body 104.

Figure 2:
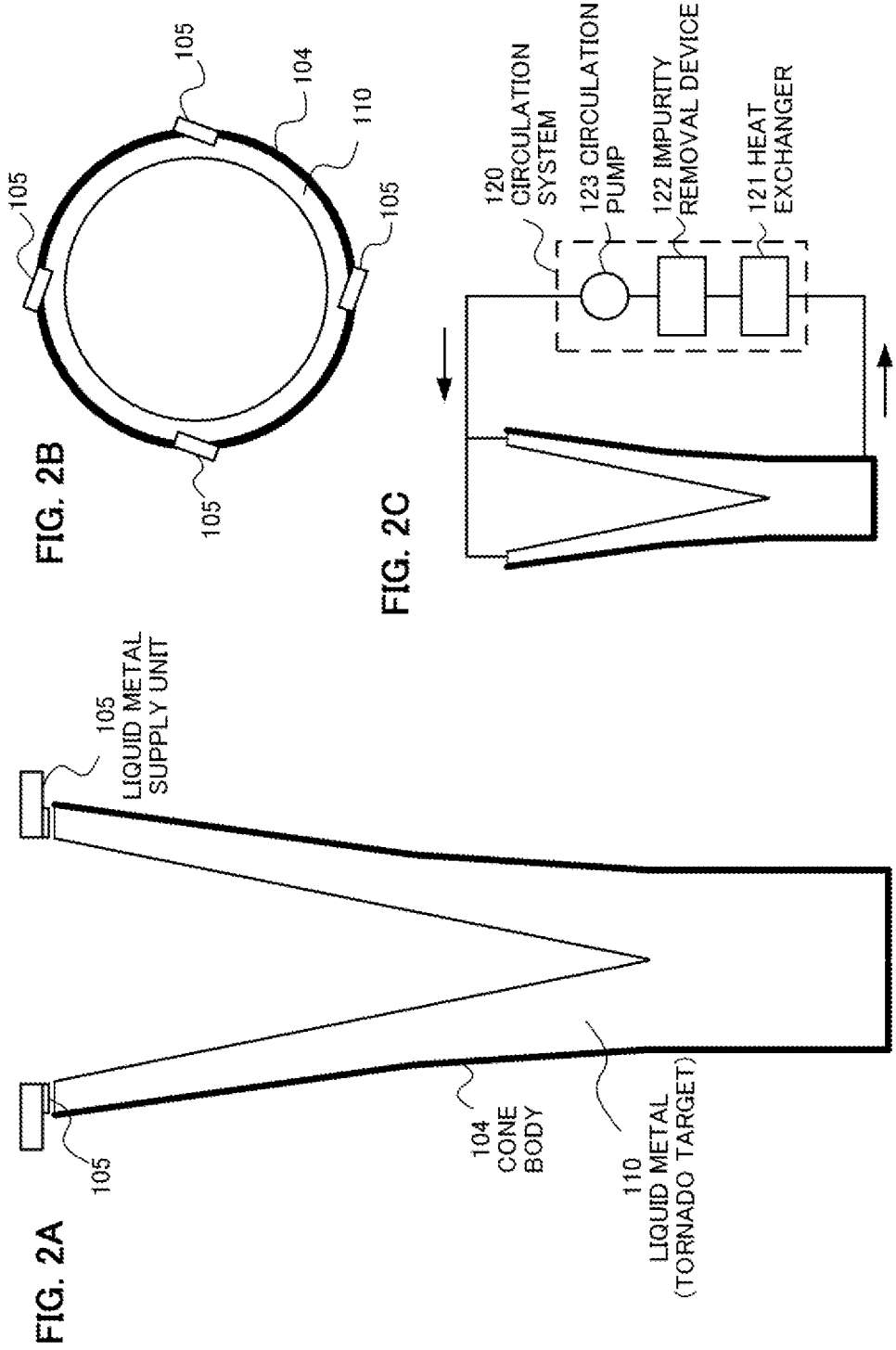
FIGS. 2A to 2C are views for explaining a shape of a cone body and liquid metal supply to the cone body.

FIG. 2A shows a vertical cross-sectional shape of the cone body 104, and FIG. 2B shows a top view of the cone body 104. As described above, the inner surface of the cone body 104 has a truncated conical portion, and a cylindrical portion. In addition, the cone body 104 is formed as thinly as possible such that the neutron generated by beam irradiation of the liquid metal is not prevented from reaching the LLFP held by the holding unit 106. Note that, in order to increase the strength and stability of the cone body 104, reinforcing rings may also be provided at several places. The supply unit 105 is provided in the vicinity of an upper end of the cone body 104. While FIG. 2B shows an example in which four supply units 105 are provided at positions 90 degrees apart from each other, the number of supply units 105 may be any number as long as the liquid film can be formed on the entire inner surface of the cone body 104.

FIG. 2C is a view for explaining the circulation system 120 for circulating the liquid metal. The liquid metal discharged to the outside via the discharge port 109 and the liquid metal outlet 107 of the cone body 104 is resupplied to the liquid metal inlet 108 by the circulation pump 123. During the circulation, the liquid metal is cooled by the heat exchanger 121, and an impurity is removed by the impurity removal device 122.

Figure 3:
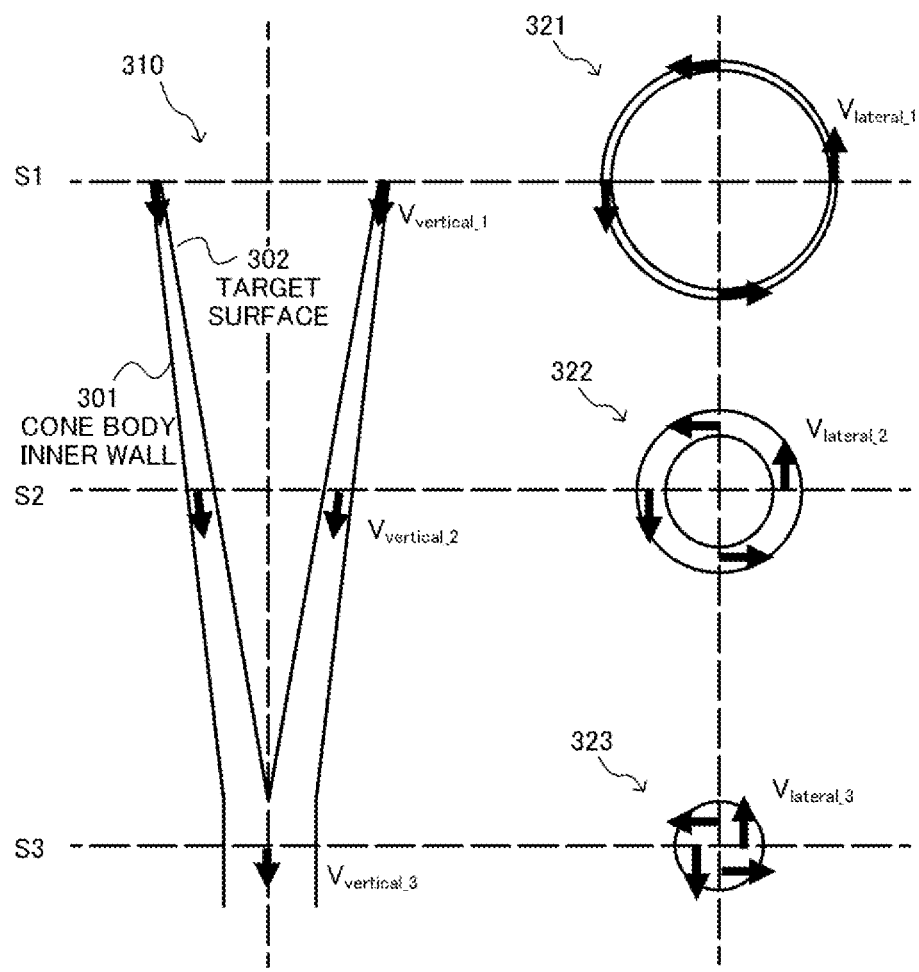
FIG. 3 is a view for explaining a design method of an inner surface shape of the cone body.

FIG. 3 is a view for explaining a design method of the inner surface shape of the cone body 104. FIG. 3 shows a vertical cross-sectional shape 310 of the cone body 104, and horizontal cross-sectional views 321, 322, and 333 at an upper end portion, a middle portion, and a lower end portion of the cone body 104. 301 denotes the inner surface of the cone body 104, and 302 denotes the surface of the liquid metal film. In addition, $V_{verticali}$ denotes the velocity of a fluid along a vertical direction, $V_{laterali}$ denotes the velocity of the fluid along a lateral direction, and $S_i$ denotes an area of the fluid on each cross section.

The shape of the inner surface of the cone body 104 is designed as a shape which allows the liquid film surface of the liquid metal formed by the supply unit 105 to have a conical shape. Consequently, the shape of the liquid film surface of the liquid metal, more specifically its inclination angle is determined first. The inclination angle is determined from the intensity of an introduced beam and properties of the liquid metal such that the irradiation intensity of the beam per unit area of the liquid film becomes an irradiation intensity which does not cause boiling of the liquid metal.

Next, it is assumed that the individual cross sections have the same $V_{vertical}$, and the shape (inclination angle) of an inner wall of the cone body 104 is determined such that the individual cross sections have the same S. As shown in FIG. 3, the inclination of the inner surface of the cone body 104 is gentler than the inclination of the target (liquid film). In addition, strictly speaking, the inner surface 301 of the cone body 104 has a tapered shape which is reduced in diameter toward the tip (lower side), and its taper angle is reduced toward the tip. Note that, herein, calculation is performed on the assumption that influences by friction and gravity are ignored and the individual cross sections have the same $V_{vertical}$. However, more strictly speaking, it is preferable to design the shape based on the fluid velocity in which these influences are taken into consideration.

Note that the liquid film surface of the liquid metal is made conical in the case where the profile of the beam intensity is constant irrespective of a distance from the center. In the case where the beam intensity has a profile in which the beam intensity decreases with distance from the center, in order to make the beam intensity per unit area of the liquid film constant, a tapered shape in which the inclination angle of the liquid film surface is gradually increased may also be used. According to this shape, the shape of the inner surface of the cone body 104 is appropriately determined.

<Effect>

Hereinbelow, a description will be given of advantageous effects of the beam target system according to the present embodiment.

FIGS. 4A to 4C are views for explaining that it is possible to increase the irradiation area of the beam applied to the target in the present embodiment. FIG. 4A shows the case where the liquid metal is caused to fall freely, FIG. 4B shows the case where the liquid metal is caused to flow along an inclined plate, and FIG. 4C shows the case where the liquid metal is caused to flow helically along the inner surface of the cone body 104, as in the present embodiment. When d denotes the diameter of the beam to be emitted, the irradiation area in the case of FIG. 4A is given by $\pi (d/2)^2$. On the other hand, the irradiation area in the case of each of FIG. 4B and FIG. 4C is given by $\pi (d/2)^2/\sin\theta$. Herein, $\theta$ is the inclination angle of each of the inclined plate and the cone.

The irradiation area in the case where the inclined plate is used (FIG. 4B) and the irradiation area in the present embodiment (FIG. 4C) are equal to each other. However, the length of the target is d/sine in the case of the former, and is d/(2×sine) in the case of the latter, and hence the present embodiment has an advantage that it is possible to reduce the size of a device.

In addition, while the LLFP can be disposed only behind the inclined plate in the method of FIG. 4B, it is possible to dispose the LLFP in an entire area around the cone body 104 in the present embodiment. Accordingly, it is possible to efficiently use the generated neutron and efficiently perform the nuclear transmutation of the LLFP.

Further, pressure in the liquid metal is increased by centrifugal force caused by the helical flow, and hence the boiling point rises and it is possible to prevent boiling of the liquid metal by the beam irradiation. As described in the conventional art, centrifugal force is generated even when the liquid metal is caused to flow along the curved plate, but larger centrifugal force is obtained by the helical flow in the present embodiment and the effect of suppressing boiling is high.

FIGS. 5A to 5D are views for explaining evaluation of target heat generation by a deuteron beam (100 MeV/u) which uses a radiation simulation. FIG. 5A is a view showing a target system, and 501 denotes a liquid lithium target and 502 denotes the cone body. FIG. 5B shows the track (amount of flow) of the deuteron beam, and FIG. 5C shows the track (amount of flow) of the neutron. As shown in FIG. 5B, the deuteron beam is stopped by the liquid lithium target almost completely. In addition, as shown in FIG. 5C, it can be seen that a sufficient number of neutrons are emitted also from a side surface of the cone body.

FIG. 5D is a view showing a heat generation distribution of the target. In each of the case of the cone-shaped target in the present embodiment and the case of a cylindrical target, the amount of heat generation was evaluated by a simulation for a beam intensity of 100 MeV/u and a beam intensity of 40 MeV/u. Each of graphs 511 and 512 denotes the amount of heat generation in the case where the beam of 100 MeV is applied to each of the cone-shaped target and the cylindrical target. In addition, each of graphs 521 and 522 shows the amount of heat generation in the case where the beam of 40 MeV is applied to each of the cone-shaped target and the cylindrical target. The horizontal axis indicates a depth [cm] from the liquid lithium surface, and the vertical axis indicates the amount of heat generation [kW/cc]. It can be seen that, for each of the beam intensities, local heat generation at an end of a range of the beam (z=about 37 cm and z=about 8 cm) can be reduced more in the case of the present embodiment than in the case of the cylindrical target which is a comparative example. That is, it can be seen that, in the present embodiment, gas generation by explosive boiling of the liquid lithium can be suppressed.

FIGS. 6A and 6B are views for explaining evaluation of nuclear transmutation efficiency of the LLFP by a simulation. FIG. 6A is a view showing the placement of liquid metal 601, a cone body 602, and LLFP 603. As the LLFP, palladium subjected to even-odd separation ($^{105}$Pd, $^{107}$Pd) is used. As shown in the drawing, the LLFP 603 is disposed around the cone body 602, and is subjected to the nuclear transmutation with high-intensity neutrons generated in the liquid metal target. FIG. 6B shows an energy distribution of the neutron emitted to the outside of the liquid metal target. It can be seen that about one neutron is generated per deuteron of 100 MeV/u.

In addition, when the deuteron beam of 1A is emitted, a nuclear transmutation number per deuteron is about 0.7, and a nuclear transmutation amount is estimated to be 25 kg a year by calculation. Thus, by using one accelerator, it is possible to perform the nuclear transmutation (detoxification) of as much as 25 kg of palladium a year, which is efficient.

[Modification]

In the present embodiment, powder of the LLFP may be mixed with the liquid metal supplied by the supply unit 105. The LLFP is positioned at a place closest to the generation position of the neutron by the beam irradiation, and the nuclear transmutation of the LLFP is thereby performed efficiently.

In addition, in the present embodiment, the cone body 104 may be formed of the LLFP (e.g., $^{93}$Zr). The cone body 104 is also positioned at a place close to the generation position of the neutron, and the nuclear transmutation of the LLFP is efficiently performed.

Further, in the present embodiment, the neutron generated by the beam irradiation of the liquid metal is used for the nuclear transmutation of the LLFP, but the target substance to be subjected to the nuclear transmutation with the neutron is not limited to the LLFP, and the substance may also be any substance.

Second Embodiment

Figure 7:
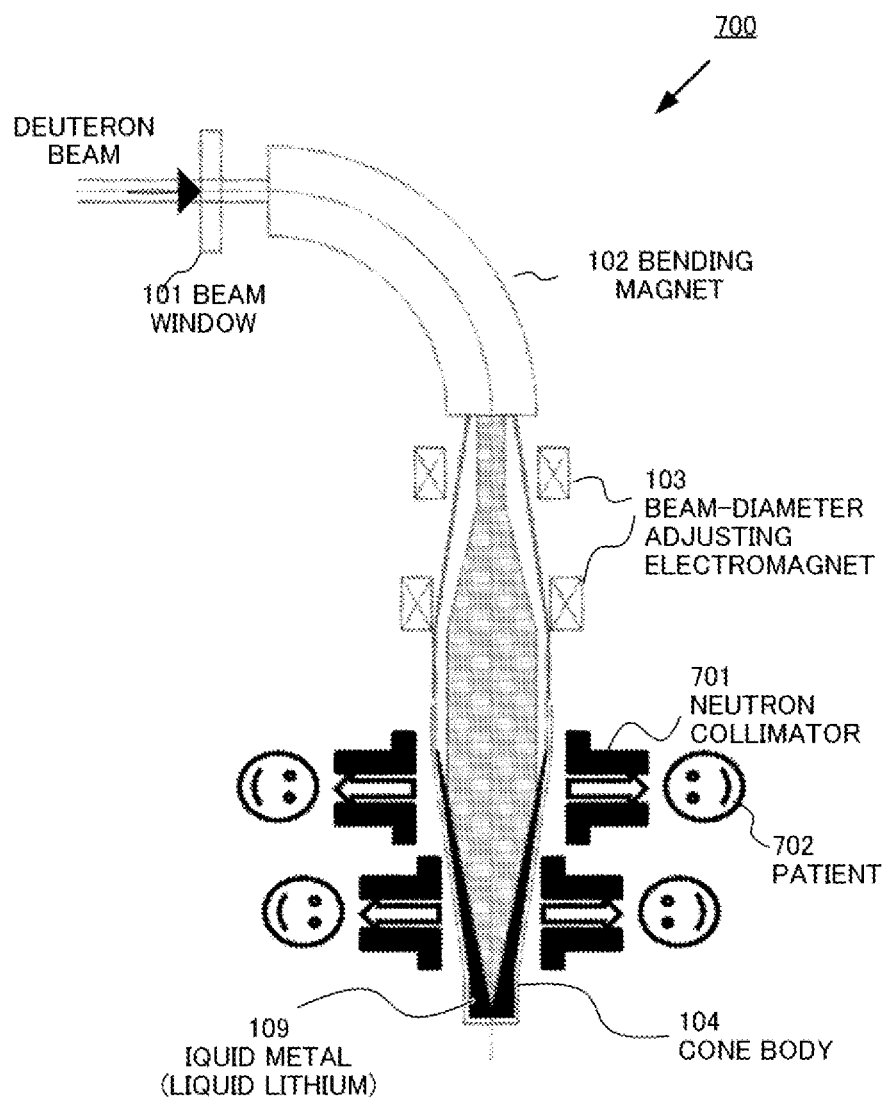
FIG. 7 is a view showing an overall structure of a beam target system (second embodiment) used in a multiple-patient type BNCT therapy system.

The present embodiment is a beam target system used in a multiple-patient type BNCT therapy system which allows boron neutron capture therapy (BNCT) for a plurality of patients. FIG. 7 shows an overall structure of a beam target system 700 according to the present embodiment. Note that the description of the circulation system of the liquid metal is omitted in FIG. 7.

While the basic structure of the beam target system 700 according to the present embodiment is similar to that of the first embodiment, the holding unit 106 for holding the LLFP around the cone body 104 is not provided, and a plurality of neutron collimators 701 are provided. The neutron collimator 701 parallelizes the neutron generated by the beam irradiation of the liquid metal, and outputs the neutron toward a subject to be irradiated (patient). The cone body 104 has the truncated conical shape, and hence the neutron collimator 701 outputs the neutron in a direction orthogonal to the beam irradiation direction. It is possible to provide a plurality of the neutron collimators 701 in a circumferential direction of the cone body 104 or in the beam irradiation direction.

According to the present embodiment, it is possible to apply the neutron to a plurality of patients. Consequently, it becomes possible to perform more efficient therapy. In addition, the output direction of the neutron is orthogonal to the beam irradiation direction, and hence the patient can be placed off the irradiation line of the beam, and safety is increased.

Note that, herein, the description has been made by using the BNCT as an example, but the structure similar to that described above can be adopted also in an inspection system in which generated neutron rays are used in non-destructive inspection.

Third Embodiment

The present embodiment is a beam target system used in a system which generates a large amount of astatine-211 ($^{211}$At). Astatine-211 is a radioactive nuclide which emits alpha rays, and is administered orally or by intravenous administration to be used in RI internal therapy in which the alpha rays are directly emitted from a focus portion of cancer.

Figure 8:
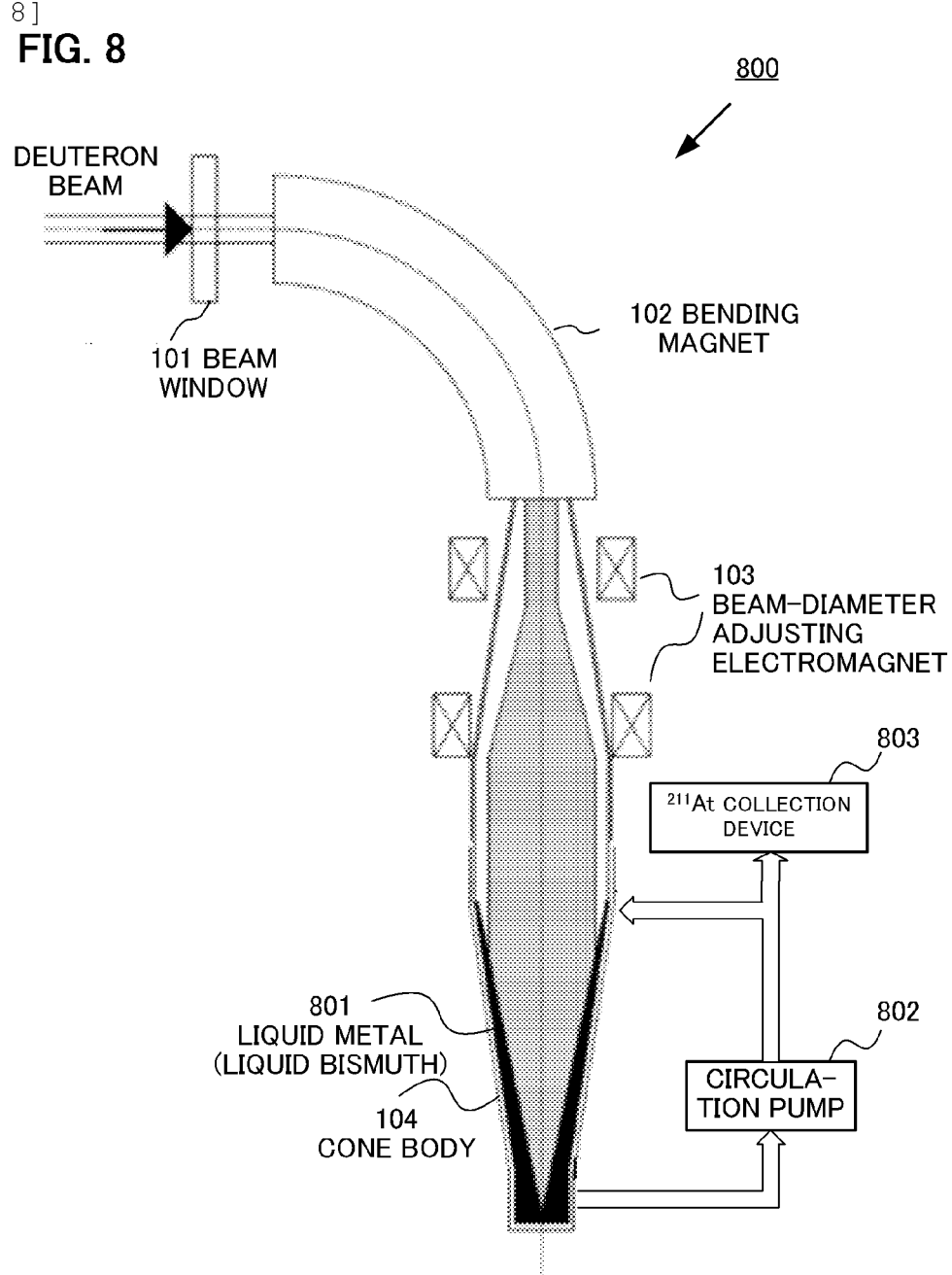
FIG. 8 is a view showing an overall structure of a beam target system (third embodiment) used in a large-amount generation system of astatine-211.

FIG. 8 is a view showing an overall structure of a beam target system 800 according to the present embodiment. Astatine-211 is generated by applying a helium beam accelerated by an accelerator (to 7.2 MeV/u) to bismuth (Bi) to thereby perform nuclear transmutation ($^{4}He+Bi \rightarrow ^{211}At+X$). Accordingly, in the present embodiment, the supply unit 105 irradiates the inner surface of the cone body 104 with liquid bismuth.

The liquid bismuth is circulated by a circulation pump 801. Astatine generated by the beam irradiation is collected together with the liquid bismuth from a lower portion of the cone body 104. The boiling point of astatine is lower than that of bismuth, and hence it is possible to separate only astatine as gas and extract astatine by a collection device 803.

According to the present embodiment, it is possible to efficiently generate a large amount of astatine-211.

REFERENCE SIGNS LIST

- 100 Beam target system
- 101 Beam window
- 102 Bending magnet
- 103 Beam-diameter adjusting electromagnet
- 104 Cone body
- 105 Liquid metal supply unit
- 106 LLFP holding unit
- 107 Liquid metal outlet
- 108 Liquid metal inlet
- 109 Discharge port
- 110 Liquid metal (liquid film)
- 120 Circulation system
- 121 Heat exchanger
- 122 Impurity removal device
- 123 Circulation pump

The invention claimed is:

1. A system for transmuting long lived fission products, comprising:
   - a neutron generation target;
   - a vertically oriented cone body having a tapered inner surface narrowing to a tip at a bottommost end of the cone body;
   - a nozzle positioned at a top end of the cone body and configured to provide a liquid metal film to the inner surface, the liquid metal film flowing in a helical direction; and
   - a proton beam source configured to irradiate the liquid metal film with a beam of protons directed along an axis of the cone body from the top end toward the tip,
   - wherein an angle of the inner surface with respect to the axis of the cone body provides an equal amount of the liquid metal film for each cross section of the cone body.

2. The system according to claim 1, wherein the cone body is made of the long lived fission products.

3. The system according to claim 1, wherein the liquid metal contains powder of the long lived fission products.

4. The system according to claim 1, wherein the liquid metal is liquid lithium, liquid bismuth, liquid sodium, liquid mercury, or liquid lead bismuth.

5. The system according to claim 1, wherein the cone body comprises stainless steel.

6. The system according to claim 1, wherein the long-lived fission products are palladium-107 ($^{107}Pd$), cesium-135 ($^{135}Cs$), zirconium-93 ($^{93}Zr$), or selenium-79 ($^{79}Se$).

* * * * *